United States Patent
Alasaarela et al.

(10) Patent No.: US 10,441,166 B2
(45) Date of Patent: Oct. 15, 2019

(54) APPARATUS AND METHOD FOR NON-CONTACT EXAMINATION OF EYE

(71) Applicant: OPTOMED OY, Oulu (FI)

(72) Inventors: Ilkka Alasaarela, Merikarvia (FI); Ilkka Jolma, Oulu (FI); Markku Virta, Kempele (FI); Seppo Rönkkö, Oulu (FI)

(73) Assignee: OPTOMED OY, Oulu (FI)

( * ) Notice: Subject to any disclaimer, the term of this patent is extended or adjusted under 35 U.S.C. 154(b) by 0 days.

(21) Appl. No.: 15/880,909

(22) Filed: Jan. 26, 2018

(65) Prior Publication Data
US 2018/0220886 A1    Aug. 9, 2018

(30) Foreign Application Priority Data

Feb. 8, 2017    (FI) ..................................... 20175110

(51) Int. Cl.
*A61B 3/12* (2006.01)
*G02B 27/00* (2006.01)
*A61B 3/14* (2006.01)

(52) U.S. Cl.
CPC .................. *A61B 3/12* (2013.01); *A61B 3/14* (2013.01); *G02B 27/0025* (2013.01)

(58) Field of Classification Search
CPC ........... A61B 3/14; A61B 3/0025; A61B 3/12; A61B 3/102; A61B 3/0058
USPC ........................................................ 351/206
See application file for complete search history.

(56) References Cited

U.S. PATENT DOCUMENTS

| | | | |
|---|---|---|---|
| 4,322,137 A | 3/1982 | Nohda | |
| 2010/0295985 A1* | 11/2010 | Matsusaka | G02B 15/177 348/345 |
| 2012/0224142 A1 | 9/2012 | Cornsweet et al. | |
| 2013/0135584 A1 | 5/2013 | Alasaarela et al. | |
| 2015/0002817 A1* | 1/2015 | Alasaarela | A61B 3/12 351/208 |
| 2015/0009473 A1 | 1/2015 | Su | |

FOREIGN PATENT DOCUMENTS

EP    2 901 919    8/2015

OTHER PUBLICATIONS

Search Report for FI 20175110, dated Oct. 18, 2017, 6 pages.
Search Report issued in EP Appln. No. 18154311.7 dated Jul. 17, 2018.

* cited by examiner

*Primary Examiner* — Mohammed A Hasan
(74) *Attorney, Agent, or Firm* — Nixon & Vanderhye P.C.

(57) ABSTRACT

An apparatus for non-contact examination of an eye comprises for illuminating and imaging the eye: an apparatus objective of a positive optical power and a positive spherical aberration which illuminates and images an angle wider than a cross section of the zone I of the retinal vasculature, the apparatus objective being common to the imaging and the illumination the optical paths of which are deviated from each other in the examination apparatus; and a secondary lens unit, which is located behind the apparatus objective in the optical path in a direction of the imaging, modifies at least one of the following optical features: lateral color aberration, astigmatism, field curvature and coma caused by the apparatus objective, and focuses the imaging radiation modified by the secondary lens unit on an image sensor for forming an image of a retina of the eye.

15 Claims, 4 Drawing Sheets

APPARATUS AND METHOD FOR NON-CONTACT EXAMINATION OF EYE

This application claims priority to FI Patent Application No. 20175110 filed Feb. 8, 2017, the entire content of which is hereby incorporated by reference.

FIELD

The invention relates to an apparatus and a method for non-contact examination of an eye.

BACKGROUND

The optical design of a fundus camera contains several challenging requirements: The image needs to be sharp and evenly illuminated with brightness high enough to overcome noise in detection. The field-of-view should be wide enough to capture a large section of the retina. And practically the whole retina should be covered with as few images as possible. It is also desirable that imaging can be performed with undilated pupils, i.e. in a non-mydriatic way also in the case of children and babies. Often the examination should be done by a hand-held device in a non-contact manner. Finally, the device should typically be compact and easy to align with the eye during the imaging, and the working distance needs to be long enough.

In the prior art, these problems have not been fully overcome. Therefore, there is a clear need to improve the ophthalmoscopic camera.

BRIEF DESCRIPTION

The present invention seeks to provide an improvement in the ophthalmoscopic imaging. According to an aspect of the present invention, there is provided an apparatus of non-contact examination of an eye as specified in claim 1.

According to another aspect of the present invention, there is provided a method of non-contact examination of an eye in claim 14.

The invention has advantages. Good quality images of a wide angle can be captured with a non-contact examination apparatus from fundus of an eye.

LIST OF DRAWINGS

Example embodiments of the present invention are described below, by way of example only, with reference to the accompanying drawings, in which FIG. 1 illustrates an example of a non-contact eye examination apparatus of a fundus of an eye;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide one or more embodiments of combined features. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for examination and/or controlling are irrelevant to the actual invention. Therefore, they need not be discussed in more detail here.

Figure 1:
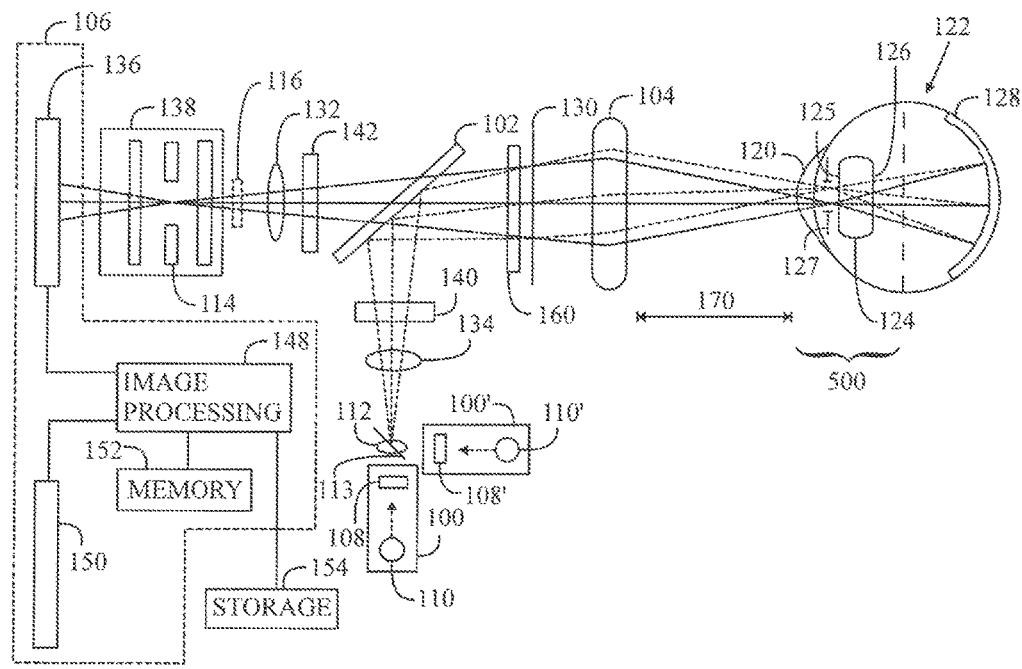

FIG. 1 illustrates an example of a non-contact eye examination apparatus of a fundus of an eye 122. The example in FIG. 1 is a simplified architecture showing elements and functional entities, whose implementation may vary. In an embodiment, the apparatus or the examination instrument may be portable. In an embodiment, the apparatus may be hand-held.

Although FIG. 1 shows rather many parts of the apparatus, only a few can be considered at first. The examination apparatus comprises, for illuminating and imaging the eye 122, an apparatus objective 104. The apparatus objective 104 is common to the imaging and the illumination optical paths 132, 134 which are deviated from each other in the examination apparatus (dashed line from exit pupil 112 refers to illumination and continuous line between retina 128 and image sensor 136 refers to imaging). The apparatus objective 104 has a positive optical power and a positive spherical aberration. The positive spherical aberration is associated with an exit pupil 112 of visible light illumination. The same is true for infrared light. In an embodiment, the apparatus objective 104 has an image plane of the exit pupil 112 of the illumination between the cornea 120 and the retina 128. In an embodiment, the apparatus objective 104 has the image plane of the exit pupil 112 of the illumination in the frontal section 500 of the eye 122. The image of the exit pupil 112 of the illumination on said image plane is distorted by the positive spherical aberration. The exit pupil 112 of the illumination refers to the exit pupil of the illumination unit 100, 100'. The image on the image plane is distorted with respect to an image that can be formed on the basis of paraxial imagery.

Correspondingly, the positive spherical aberration is associated with the exit pupil 112 of any other optical radiation used in the examination. The exit pupil 112 is common to both light sources 110, 110' for simplicity but they may also differ in real examination apparatuses.

The positive spherical aberration may be defined such that peripheral rays of light bent to an optical axis of the apparatus objective 104 at a point which is closer to the apparatus objective 104 than the point at which rays of light more adjacent to the optical axis bent. The peripheral rays refer to the rays which are farther from the optical axis than the axial rays in the radial direction of the apparatus objective 104. A person skilled in the art considers the spherical aberration perhaps the most harmful and undesirable of all optical aberrations but this application explains how to utilize it.

The apparatus objective 104 with the positive spherical aberration enables illumination and imaging of the retina 128 in an angle wider than a cross section of the zone I of the retinal vasculature.

The inner retinal surface of the eye 122 is divided in three concentric circles of which zone I is around the optic disc. The radius of the zone I may be defined as about two times the distance between the center of the optic disc and the center of the macula.

The examination apparatus further comprises a secondary lens unit 138, which is located behind the apparatus objective 104 in the optical path in a direction of the imaging. The secondary lens unit 138 modifies at least one optical feature related to the image of the retina 128 which is formed on the image sensor 136. The modified features include lateral color aberration caused by the apparatus objective 104, astigmatism caused by the apparatus objective 104, field curvature caused by the apparatus objective 104 and coma caused by the apparatus objective 104. The secondary lens unit 138 also focuses the modified imaging radiation on an image sensor 136 for forming an image of a retina 128 of the eye 122. The secondary lens unit 138 may reduce the lateral color aberration, the astigmatism and correct the coma. The secondary lens unit 138 may change or refigure the field curvature of a formed image. Any or all of these modifications may improve the image quality such as resolution and distortion.

The apparatus objective 104 has an image plane of an entrance pupil 114 of the imaging between the cornea 120 and the retina 128. In an embodiment, the image of the pupil 114 of secondary lens unit 138 may be formed in the frontal section 500 of the eye 122. The image of the entrance pupil 114 on said image plane is distorted by the positive spherical aberration. The entrance pupil 114 of the imaging refers to the entrance pupil 114 of the secondary lens unit 138. The positive spherical aberration is also associated with an entrance pupil 114 of the secondary lens unit 138, the entrance pupil 114 being a physical aperture related to imaging.

The secondary lens unit 138 may also reduce or correct the positive spherical aberration of the image of the retina 128 formed on the image sensor 136, the positive spherical aberration being caused by the apparatus objective 104.

The apparatus may comprise a first illumination unit 100 which may be for illumination with visible light, a second illumination unit 100' which may be for illumination with infrared light, a main beam splitter 102, and a camera unit 106. Instead of the main beam splitter 102 one or more mirrors may be used to reflect illumination towards the objective 104 and the eye 122. The illumination unit 100 of visible light comprises a lens or lenses 108 and a visible light source 110 which may, in turn, comprise one or more source elements. The illumination unit 100' of infrared light comprises a lens or lenses 108' and a infrared light source 110' which may, in turn, comprise one or more source elements.

A source beam splitter 113 may direct both optical lights from the illumination unit 100, 100' to the main beam splitter 102. The exit pupil 112 is a physical aperture or an image of a physical aperture in the illumination unit 100, 100' formed by the optical elements after the aperture.

However, the illumination units 100, 100' are not limited to this example but may in general transmit at least one of the following: ultraviolet light (about 250 nm to 400 nm), visible light (about 400 nm to 700 nm), and infrared light (about 700 nm to 1400 nm).

The illumination unit 100 and/or 100' may direct optical radiation of the source 110, 110' from an exit pupil 112 of the illumination unit 100, 100' to the main beam splitter 102. The main beam splitter 102 directs by the reflection the optical radiation to the apparatus objective 104 in an optical path 134 of illumination radiation. An optical path of optical radiation may be defined as a volume occupied by the optical radiation. The size and shape of the path depends on the properties of lenses and other optical elements. The eye 122 may also have some effect on the path.

In general, a beam splitter (main beam splitter or source beam splitter) reflects a part of the optical radiation directed to it and allows a remaining part of the optical radiation to pass through it. Often a beam splitter splits a beam of optical radiation into two such that both beams have about the same intensity which may range from a few percents or less to almost 50% of the intensity of the original non-split beam.

In an embodiment, the main beam splitter 102 may comprise a polarizer. The main beam splitter 102 with a polarizer may be a polarizing beam splitter, for instance. Alternatively or additionally, there may be one or more polarizers 140, 142 for polarizing both the illumination radiation and the imaging radiation. The polarizer associated with the main beam splitter 102 may cause the optical radiation to be linearly polarized. Polarized light may be used for reducing undesirable reflection from the eye 122 and optical elements of the apparatus.

If the main beam splitter 102 comprises a polarizer, the optical radiation reflected from the main beam splitter 102 to the apparatus objective 104 is polarized. The polarized optical radiation then propagates to the retina 128 of the eye 122 and is reflected from the retina 128. Since the surface of the retina 128 is optically rough, the polarized optical radiation becomes at least partly depolarized. When the reflected optical radiation in the imaging direction hits the main polarizing beam splitter 102, the polarized part of the optical radiation is reflected from the main beam splitter 102 towards the illumination unit 100 without being detected. However, a part of the depolarized part of the reflected optical radiation propagates through the main beam splitter 102 towards the image sensor 136.

In addition to or instead of a polarization beam splitter, a beam splitter with a pre-polarizer 140 for the illumination radiation and a post-polarizer 142 for the imaging radiation may be used. The pre-polarizer 140 may perform a linear polarization to the illuminating optical radiation 134 before the main beam splitter 102. The post-polarizer 142 may also be a linear polarizer and it may be in a crossed position with respect to the pre-polarizer 140 i.e. the polarization axis of the post-polarizer 142 is turned 90° with respect to that of the pre-polarizer 140. In this configuration, any optical radiation having a linear polarization that passes the pre-polarizer 140 may not pass the post-polarizer 142. Thus, reflections from the apparatus objective 104, for example, may not pass the post-polarizer 142 and hence may not propagate to the image sensor 136. However, a part of the depolarized optical radiation reflected from the retina 128 may pass through the post-polarizer 142 up to the image sensor 136.

The apparatus objective 104, which may comprise one or more lenses, may have a designed property of forming a real image of the exit pupil 112 of the illumination unit 100 in a position ranging from the cornea 120 to the backside 126 of the crystalline lens 124 of the eye 122 for illuminating the retina 128 of the eye 122 with optical radiation when the examination instrument is moved to a working distance 170 from the eye 122. Similarly, the apparatus objective 104 may have a designed property of forming a real image of the entrance pupil 114 of the secondary lens unit 106 in a position ranging from the cornea 120 to the backside 126 of the crystalline lens 124 of the eye 122 when the examination instrument is moved to the working distance 170 from the eye 122. Illuminating light may pass the pupil 127 of the eye 122 when propagating to the retina 128. Similarly, the imaging optical radiation travelling towards the image sensor 136 may pass through the pupil 127 of the eye 122.

In an embodiment, the apparatus objective 104 may also have a designed property of forming a real intermediate image 130 of the retina 128 between the apparatus objective 104 and the image sensor 136 in a path 132 of the imaging radiation which is the optical radiation reflected from the retina 128. In an embodiment, the real intermediate image 130 may be between the apparatus objective 104 and the main beam splitter 102. In another embodiment, the real intermediate image 130 may be between the apparatus objective 104 and the secondary lens unit 138 such that the real intermediate image 130 is between the main beam splitter 102 and the secondary lens unit 138. However, no intermediate image is necessary.

The main beam splitter 102 may direct the optical radiation from the retina 128 to the image sensor 136. In FIG. 1, the main beam splitter 102 passes a part of the optical radiation through towards detection. The main beam splitter 102 may have been designed and/or positioned such that the main beam splitter 102 causes the path 134 of the illumination radiation and the path 132 of the imaging radiation to deviate from each other in a predetermined manner. The deviation may prevent an overlap of the images and/or beams of radiation of the exit pupil 112 and the entrance pupil 114 at least in the crystalline lens 124 (see FIG. 3).

The main beam splitter 102 may reside between the apparatus objective 104 and an aperture 116 of the secondary lens unit 138. The main beam splitter 102 may be located between the entrance pupil 114 of the secondary lens unit 138 and the apparatus objective 104. The main beam splitter 102 may reside between the intermediate image 130 and the secondary lens unit 138. The main beam splitter 102 may form a deviation between the illuminating optical radiation and the imaging radiation. For example, a location optically halfway between the entrance pupil 114 of the secondary lens unit 138 and the intermediate image 130 may be possible for the main beam splitter 102. Some distance between the intermediate image 130 and the main beam splitter 102 may be good for avoiding possible dust on the main beam splitter 102 to become visible in the images, for example.

Although the main beam splitter 102 is described here to be transmissive for the imaging path 132 and reflective for the illumination path 134, it can be used in an opposite way by reflecting the imaging path 132 and transmitting the illumination path 134.

The camera unit 106 comprises an image sensor 136 and may comprise the secondary lens unit 138 at least partly. The secondary lens unit 138 may also be a separate component from the camera unit 106.

The secondary lens unit 138 may comprise at least two lenses. The secondary lens unit 138 may form a real image of the retina 128 on the image sensor 136 with the light reflected from the retina 128 of the eye 122. The reflected light may or may not form the intermediate image 130 before the image sensor 136. The image sensor 136 may comprise pixels which may be in the form of a matrix. The purpose of the image sensor 136 may be to transform the optical image into an electric form. However, the image sensor 136 may also be a photographic film instead of an optoelectronic detector. The image sensor 136 may be a CCD (Charged-Coupled Device) cell or a CMOS (Complementary Metal Oxide Semiconductor) cell.

In an embodiment, the examination apparatus may have focusing means for either manual or automatic focusing operation for the image.

The camera unit 106 may function like a digital camera. The image in the electric form, one or more still images or a video, may be processed in an image processing unit 148 and then presented to the user on the screen 150 of the examination instrument. The image processing unit 148 may comprise a processor and memory 152. The images of the eye 122 may be sent to an outside storage 154 where they may be stored. The images stored in the storage 154 may be retrieved therefrom for to be shown on a screen. The storage 154 may be a local databank or it may be a server in a private or public cloud.

There is a deviation between an optical axis of the path of the illumination radiation and an optical axis of the path of the imaging radiation. The angle between the directions of the optical axis of the path of the illumination radiation and the optical axis of the path of the imaging radiation may be a few degrees. The angle may be 3° to 12°, for example. The angle is caused by the beam splitter 102 (see FIG. 1) or by illumination from separate locations of the illumination unit 100, 100' and the camera unit 106 without the beam splitter (see FIGS. 2A and 2B).

Figure 2A:
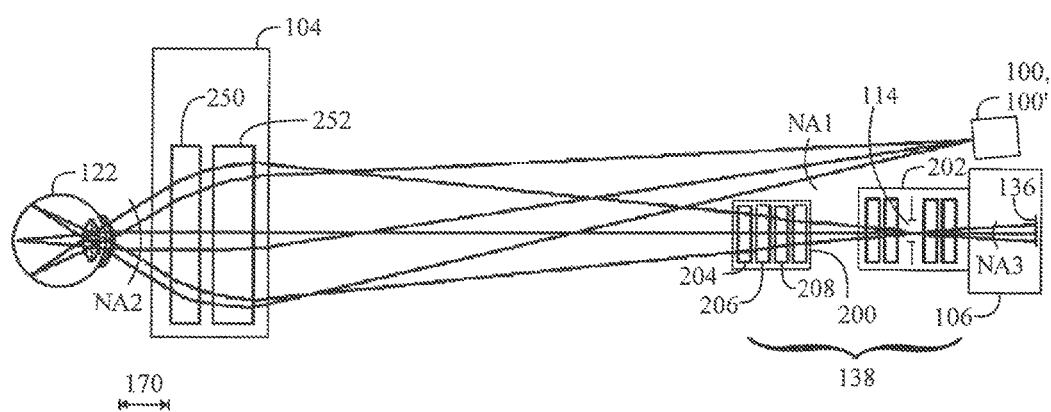
FIG. 2A illustrates another example of a non-contact eye examination apparatus of a fundus of an eye.

FIG. 2A illustrates an example of the apparatus with another optical design. In general, an objective of the camera 106 may be included in the secondary lens unit 138 as illustrated in FIG. 1. FIG. 2A illustrates an example of an embodiment where the secondary lens unit 138 comprises a corrective lens unit 200 and a camera objective 202 which is separate from the corrective lens unit 200. The apparatus objective 104 has the positive spherical aberration. In this example, the entrance pupil 114 may be associated with the camera objective 202. The spherical aberration may be associated with the entrance pupil 114 of the camera objective 202 such that, in an embodiment, the image of the entrance pupil 114 of the camera objective 202 is formed in a range between the cornea 120 and the back side 126 of the crystalline lens 124 along the optical axis. In an embodiment, the image of the entrance pupil 114 of the camera objective 202 may be formed between the cornea 120 and the retina 128. The spherical aberration has a similar effect on both the illuminating and imaging rays of light.

The camera objective 202 may be detachable or non-detachable from the camera 106. The camera unit 106 may be an integrated combination of the detecting component 136 and the camera objective 202 such that the camera unit 106 with the camera objective 202 is a commercial product as such. The camera objective 202 may form a sharp image on the image sensor 136 without additional optics at least from one distance. The camera unit 106 may be capable of focusing by moving at least one optical component such as lens of the camera objective 202 axially. The camera unit 106 may also comprise the image processing unit 148 and the screen 150 in a common frame.

The corrective lens unit 200 may locate between the apparatus objective 104 and the camera objective 202. The corrective lens unit 200 may perform the modification of at least one optical feature associated with the visible light band. Alternatively or additionally, the corrective lens unit 200 may perform the modification of at least one optical feature associated with the infrared and/or ultraviolet light band. The camera objective 202 may, in turn, focus the imaging radiation modified by the corrective lens unit 200 on the image sensor 136.

In an embodiment, the apparatus objective 104 may have a designed property of forming a real image of the entrance pupil 114 of the camera objective 202 in a position ranging from the cornea 120 to the backside 126 of the crystalline lens 124 of the eye 122 when the examination instrument is moved to a working distance 170 from the eye 122.

Figure 2B:
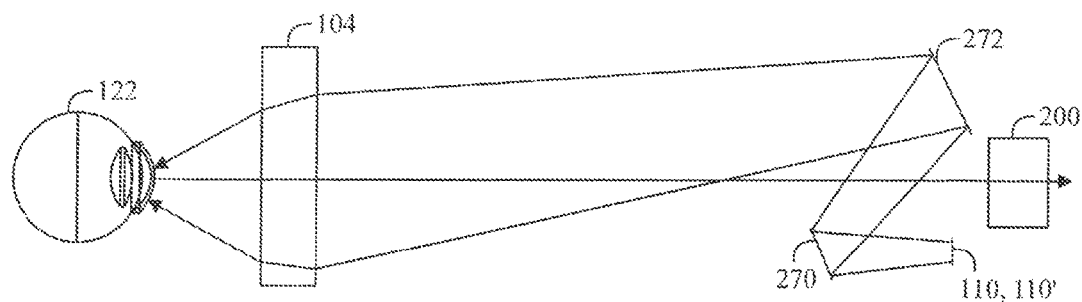
FIG. 2B illustrates an example of an embodiment, where mirrors are used to direct illumination from the one or more optical sources to the objective and the eye.

FIG. 2B illustrates an example of an embodiment, where mirrors 270 and 272 are used to direct illumination from the one or more optical sources 110, 110' to the objective 104 and the eye 122. The mirrors 270, 272 may be on both sides of the optical axis of the apparatus such the optical beam is directed to the objective 104 in an oblique angle with respect to the optical axis.

In the embodiment of FIG. 2A, no main beam splitter 102 is required because the illumination is directed in an oblique angle from the one or more illumination units 100, 100' to the apparatus objective 104 and to the eye 122. Also the use of mirrors may be avoided in the embodiment of FIG. 2A.

In an embodiment, the corrective lens unit 200 may comprise at least two sub-lens units 202, 204, 206 (FIG. 2 has four sub-lenses of which three has reference numbers) for modifying the at least one optical feature of the imaging radiation passed through the apparatus objective 104.

In an embodiment, the secondary lens unit 138 with or without the camera objective 202 and thus the corrective lens unit 200 may comprise a first lens sub-unit 204, a second lens sub-unit 206 and a third lens sub-unit 208. The first lens sub-unit 204 may reduce the lateral color aberration of the apparatus objective 104. In an embodiment, the second lens sub-unit 206 may reduce the astigmatism of the apparatus objective 104.

In an embodiment, the third lens sub-unit 208 may correct the coma of the objective lens 104 at least partly.

In an embodiment, an optical power of the corrective lens unit 200 may be in a range from −20 to 20 diopters.

In an embodiment, the first lens sub-unit 204, which is the closest lens sub-unit of the secondary lens unit 138 to the apparatus objective 104 in the optical path in the direction of the imaging, may reduce the lateral color aberration of the other of the at least two lens sub-units 206, 208.

In an embodiment, the second lens sub-unit 206 may locate between the first lens sub-unit 204 and the third lens sub-unit 208. In an embodiment, the second lens sub-unit 206 may further reduce the astigmatism of the first lens sub-unit 204.

In an embodiment, the third lens sub-unit 208 may further correct the coma of the first lens sub-unit 204 at least partly, reduce the axial color aberration of the first lens sub-unit 204, and reduce the spherical aberration of the first lens sub-unit 204.

In an embodiment, the first lens sub-unit 204 may be made of flint glass, may have positive power meniscus, and may have convex surface towards the eye 122. The first lens sub-unit 204 may create a strong lateral color aberration for compensating the opposite lateral color caused by the objective 104 and the second and third lens sub-units 206, 208.

In an embodiment, the second lens sub-unit 206 may be made of crown glass, and may have negative power. The second lens sub-unit 206 may create a strong astigmatism for compensating the opposite astigmatism caused by the objective 104 and the first lens sub-unit 204.

In an embodiment, the third lens sub-unit 208 may be made of flint glass, may have negative power meniscus, and may have a convex surface towards the eye 122. The third lens sub-unit 208 may create a strong coma for compensating the opposite coma caused by the objective 104 and the first lens sub-unit 204. In an embodiment, the third lens sub-unit 208 may also compensate axial color aberration caused by the first lens sub-unit 204. In an embodiment, the third lens sub-unit 208 may compensate spherical aberration caused by the first lens sub-unit 204.

Any lens sub-unit alone or together with at least one other lens sub-unit may modify the field curvature caused by the apparatus objective 104.

Figure 3:
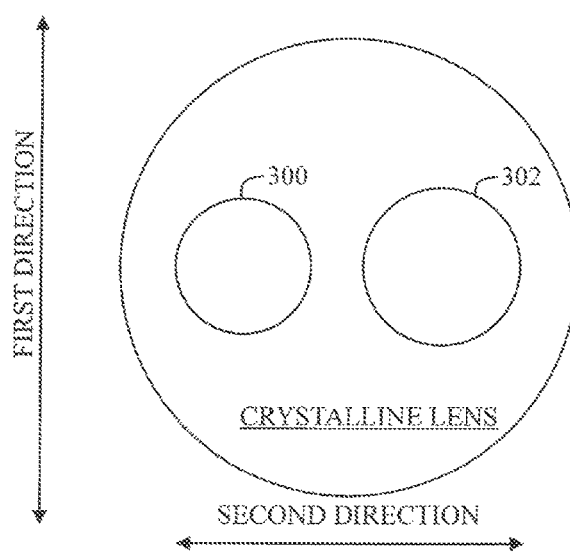
FIG. 3 illustrates an example of how illumination and imaging optical radiation are directed into the eye through the crystalline lens of the eye.

FIG. 3 illustrates an example of how illumination and imaging optical radiation are directed into the eye 122 through the crystalline lens 124 of the eye 122. The area 300 is a cross section of the path of the illumination radiation and the area 302 is a cross section of the path of the imaging radiation on a front surface 125 of the crystalline lens 124 or inside the crystalline lens 124 (see also FIG. 1).

The cross sections of the optical paths on the frontal and rear surfaces 125, 126 of the crystalline lens 124 are fully illuminated disks 300, 302 side by side. The cross sections of the optical paths are side by side in a non-overlapping manner.

Figure 4:
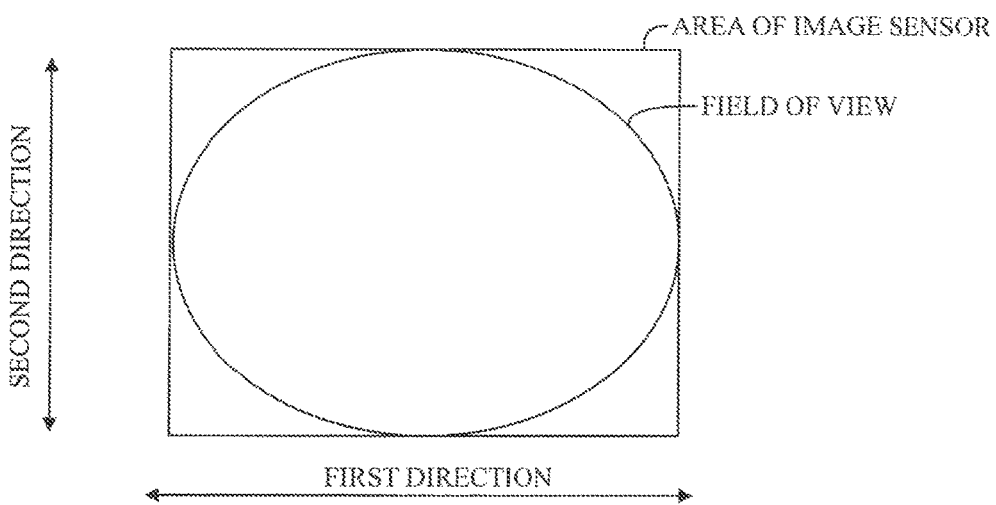
FIG. 4 illustrates an example of maximum field-of-views in two orthogonal directions.

In an embodiment an example of which is illustrated in FIG. 4, the positive spherical aberration of the apparatus objective 104, and a ratio of a focal length and a diameter of a maximum entrance pupil of the apparatus objective 104 may be set such that the maximum field-of-view is at least 65° in a first direction and less in a second direction, the first and second directions being perpendicular to each other. The entrance pupil of the apparatus objective 104 in this application refers to the entrance pupil when no other optical components are associated with the apparatus objective 104. The first and the second directions are also shown in FIG. 3. The field of view may be narrower in a direction of a line which goes through the center points of the cross sections 300, 302 of the illumination path and the imaging path.

In an embodiment, the positive spherical aberration of the apparatus objective 104, and a ratio of the a working distance 170 of the examination apparatus and a diameter of a maximum entrance pupil of the apparatus objective 104 may be set such that the maximum field-of-view is at least 65° in the first direction and less in the second direction, the first and second directions being perpendicular to each other. The working distance 170 may be between 4 mm to 20 mm, for example. That is, the examination apparatus has no contact with the eye 122. In an embodiment, the maximum field-of-view may be at least 80° in the first direction and less in the second direction. In this manner, two to four images may be required to cover the retina 128 fully or widely enough for most examination purposes in one dimension. The area of the retina 128, i.e. the retina 128 in two dimensions, may then be covered fully or widely enough with six to twelve images.

In an embodiment, an F-number of the apparatus objective 104 may range 1 to 0.5. This refers to the apparatus objective alone without other optical parts.

Figure 5:
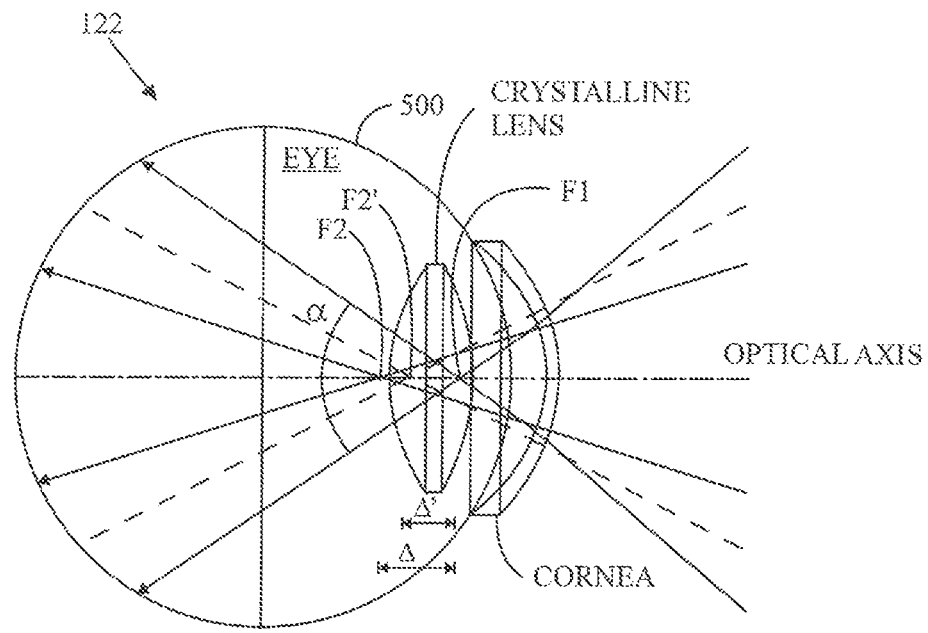
FIG. 5 illustrates an example of the positive spherical aberration of the apparatus objective.

In an embodiment an example of which is illustrated in FIG. 5, the spherical aberration of the apparatus objective 104 may separate focuses F1, F2 of axial rays and peripheral rays of the illumination and imaging in a range Δ from a half a millimeter to 10 millimeters in a direction of the optical axis. That is, the distance between the focuses F1 and F2 may be 0.5 mm to 10 mm, for example. The peripheral rays have their focus F1 closer to the apparatus objective 104 and the cornea than the axial rays.

In an embodiment, a focal length the apparatus objective 104 and a radial distance from the optical axis at which rays of optical radiation hit the apparatus objective 104 may have a determined interdependence therebetween.

In an embodiment, the focal length the apparatus objective 104 may be a desired function of the radial distance from the optical axis of the apparatus objective 104.

In an embodiment, the spherical aberration of the apparatus objective 104 may separate, in a direction of the optical axis, a focus F1 of the peripheral rays of the illumination in a first cross section of the eye 122 and a focus F2' of the peripheral rays of the illumination in a second cross section of the eye 122 in a range Δ' from about a half a millimeter to about 5 millimeters, the second cross section being perpendicular to the first cross section. That is, the distance between the focuses F1 and F2' may be 0.5 mm-5 mm, for example. The dashed lines in FIG. 5 refer to peripheral illumination rays on the second cross section a normal of which is actually perpendicular to the surface of the image. The peripheral illumination rays drawn with the dashed lines are thus rotated around the optical axis by 90° in FIG. 5 because the first cross section and the second cross section are orthogonal or approximately orthogonal to each other.

Similarly, the spherical aberration of the apparatus objective 104 may separate, in a direction of the optical axis, a focus F1 of the peripheral rays of the imaging in the first cross section of the eye 122 and a focus F2' of the peripheral rays of the imaging in the second cross section of the eye 122 in a range Δ' from about a half a millimeter to about 5 millimeters, the second cross section being perpendicular to the first cross section. That is, the distance between the focuses F1 and F2' may be 0.5 mm-5 mm, for example. The dashed lines in FIG. 5 can be used to refer, in a similar manner to the illumination, to the peripheral imaging rays on the second cross section a normal of which is perpendicular to the surface of the image. The peripheral imaging rays drawn with the dashed lines may thus interpreted to be rotated around the optical axis by 90° in FIG. 5 because the first cross section and the second cross section are at least approximately orthogonal to each other.

In an embodiment an example of which is illustrated in FIG. 5, a diameter of the entrance pupil of the apparatus objective 104 in a first direction is larger than a diameter of the entrance pupil of the apparatus objective 104 in a second direction which is perpendicular to the first direction. In this manner, the entrance pupil of the apparatus objective 104 may be rectangle or ellipse, for example.

In an embodiment which is illustrated in FIG. 2, the apparatus objective 104 may comprises a first spherical lens 250 and a second spherical lens 252. The first spherical lens 250 may have a shape factor from −3 to −0.5, and it may locate in front of the second spherical lens 252 in the direction of imaging.

In an embodiment, the second spherical lens 252 may have a shape factor from −2 to 0.5. The focal length of the second spherical lens 252 may be larger than that of the first spherical lens 250. The shape factor C may be defined mathematically as follows: $C=(R2+R1)/(R2-R1)$, where R1 is a radius of curvature of a first surface of a lens and R2 is a radius of curvature of a second surface of a lens.

In an embodiment, the apparatus objective 104 may comprise at least one non-spherical lens, but the apparatus objective 104 has to have the positive spherical aberration.

Figure 6:
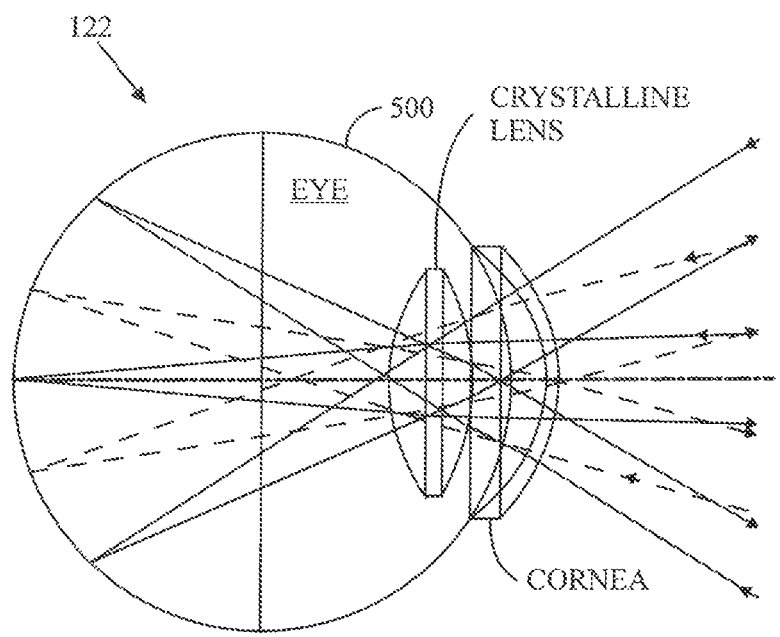
FIG. 6 illustrates an example of how illumination and imaging rays are separated in the eye.

FIG. 6 illustrates an example of how illumination and imaging rays are separated in the eye 122. The separation of the illumination and imaging rays is caused by the deviation of them by the beam-splitter 102 or the oblivious transmission of the illumination rays with respect to the imaging rays (see FIGS. 1 and 2). The waist of the illumination rays is between the back side 126 of the crystalline lens 124 and the cornea 120. The waist of the imaging rays is between the back side 126 of the crystalline lens 124 and the cornea 120.

Figure 7:
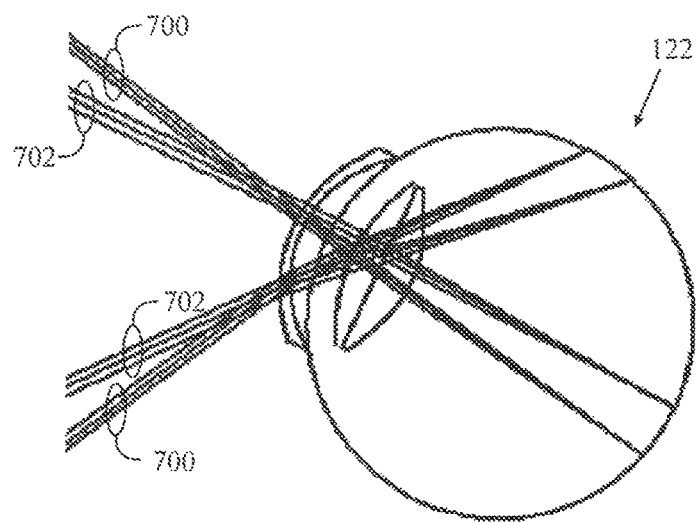
FIG. 7 illustrates an example of examining the eye from the front and at an oblique angle.

FIG. 7 illustrates an example where the eye 122 is examined from an oblique angle with respect to the optical axis of the eye 122 in order to image area of the retina decentered from the optical axis of the eye. The four set of rays represent the rays through the image of the illumination pupil from the angles corresponding the angles of the peripheral rays in the first and the second dimensions. The rays in larger angle 700 correspond to the peripheral illuminating or imaging rays in the first dimension. The rays in smaller angle 702 correspond to the peripheral illumination or imaging rays in the second dimension.

Figure 8:
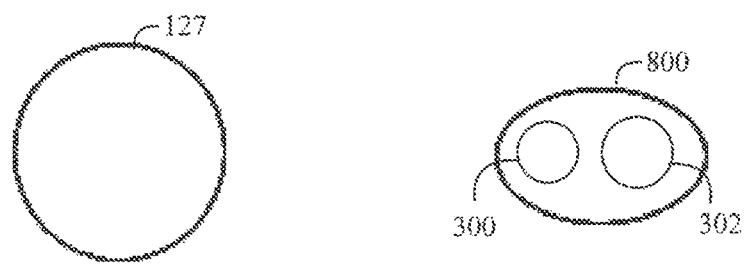
FIG. 8 illustrates examples of shapes of iris when seen from the front and at the oblique angle.

FIG. 8 illustrates an example of the pupils 127, 800 of the eye 122 seen at different angles. The pupil 127 is typically a circle when examined in the direction parallel to the optical axis of the eye 122. The pupil 800 is typically an ellipse when examined in the direction which is at an oblique angle with respect to the optical axis of the eye 122. The apparatus may be tilted such that, when the pupil 800 is examined in an oblique angle, the area 300 of the illumination beam and the area 302 of the imaging beam are at least approximately side by side in a direction of the major axis of the ellipse shaped pupil 800. The spherical aberration of the objective 104 enables convergence of the optical rays properly through the cornea 120, the narrow pupil 800 and the crystalline lens 124 which, in turn, makes a wide angle examination of the retina 128 possible.

The apparatus may be applied in the examination of retinopathy of premarity, retinoblastoma, Zika-virus related retinal changes, coat's disease or the like. Although the examination may be mydriatic, the pupil of the eye of a child is small which brings challenges to the examination. However, the apparatus objective 104 with positive spherical aberration and the secondary lens unit 138 for modifying optical aberrations caused by the apparatus objective 104 makes it easier to capture images of the retina.

Figure 9:
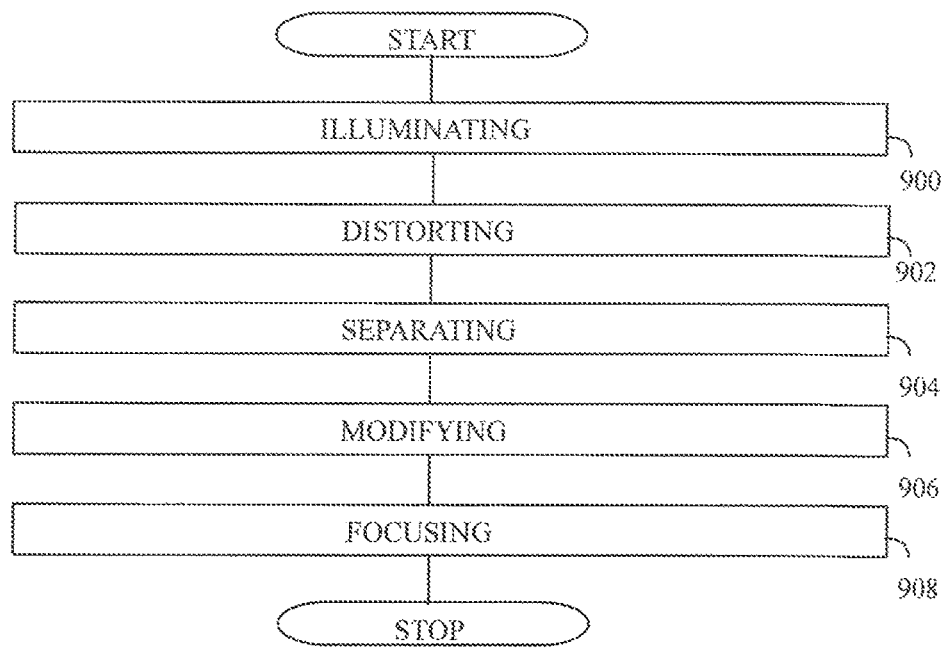
FIG. 9 illustrates of an example of a flow chart of a measuring method.

FIG. 9 is a flow chart of the measurement method. In step 900, an eye 122 is illuminated and imaged through a common apparatus objective 104 which has a positive optical power and a positive spherical aberration for covering an angle wider than a cross section of the zone I of the retinal vasculature, the imaging and the illumination having optical paths deviated from each other in the examination apparatus. In step 902, an image of an exit pupil 114 of imaging and an image of an entrance pupil 112 of illumination is distorted on their image planes in the frontal section 500 of the eye 122 by the positive spherical aberration of the apparatus objective 104. In step 904, the optical paths of imaging and illumination are separated at least on frontal and rear surfaces 125, 126 of the crystalline lens 124 by the deviation of the optical paths from each other in the examination apparatus, cross sections of the optical paths on the frontal and rear surfaces 125, 126 of the crystalline lens 124 being fully illuminated areas 300, 302 side by side. In step 906, at least one of the following optical features: lateral color aberration, astigmatism, field curvature and coma caused by the apparatus objective 104, is modified by a secondary lens unit 138 located behind the apparatus objective 104 in the optical path in a direction of the imaging. In step 908, the imaging radiation modified by the secondary lens unit 138 is focused on an image sensor 106 for forming an image of a retina 128 of the eye 122.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus for non-contact examination of an eye, wherein the examination apparatus comprises, for illuminating and imaging the eye, an apparatus objective of a positive optical power and a positive spherical aberration and a secondary lens unit;
    the apparatus objective is common to the imaging and the illumination the optical paths
    the apparatus objective is configured to have an image plane of an exit pupil of the illumination and an entrance pupil of the imaging within the eye, an image of the exit pupil of the illumination and an image of the entrance pupil on said image plane being distorted by the positive spherical aberration, and illuminate and image an angle wider than a cross section of the zone I of the retinal vasculature,
    the apparatus is configured to separate the optical paths of the imaging and illumination at least on frontal and rear surfaces of the crystalline lens by deviation of the imaging and illumination optical paths from each other, cross sections of the optical paths on the frontal and rear surfaces of the crystalline lens being fully illuminated areas side by side; and
    the secondary lens unit is located behind the apparatus objective in the optical path in a direction of the imaging, is configured to modify at least one of the following optical features: lateral color aberration, astigmatism, field curvature and coma caused by the apparatus objective, and focus the imaging radiation modified by the secondary lens unit on an image sensor for forming an image of a retina of the eye.

2. The apparatus of claim 1, wherein the secondary lens unit comprises a corrective lens unit and a camera objective, the corrective lens unit being located between the apparatus objective and the camera objective, and being configured to perform the modification of at least one optical feature, the camera objective being configured to focus the imaging radiation modified by the corrective lens unit on the image sensor.

3. The apparatus of claim 2, wherein the corrective lens unit comprises at least two sub-lens units for modifying the at least one optical feature.

4. The apparatus of claim 1, wherein the secondary lens unit comprises a first lens sub-unit, a second lens sub-unit and a third lens sub-unit;
    the first lens sub-unit is configured to reduce lateral color aberration of the apparatus objective;
    the second lens sub-unit is configured to reduce astigmatism of the apparatus objective; and
    the third lens sub-unit is configured to correct coma of the apparatus objective.

5. The apparatus of claim 4, wherein the first lens sub-unit, which is the closest lens sub-unit of the secondary lens unit to the apparatus objective in the optical path in the direction of the imaging, is further configured to reduce lateral color aberration of the other of the at least two lens sub-units.

6. The apparatus of claim 3, wherein the second lens sub-unit is located between the first lens sub-unit and the third lens sub-unit, and further configured to reduce astigmatism of the first lens sub-unit.

7. The apparatus of claim 3, wherein the third lens sub-unit is further configured to reduce coma of the first lens sub-unit, axial color aberration of the first lens sub unit, and spherical aberration of the first lens sub-unit.

8. The apparatus of claim 1, wherein the positive spherical aberration of the apparatus objective and a ratio of a focal length and a diameter of a maximum entrance pupil of the apparatus objective are set such that the maximum field-of-view is at least 65□ in a first direction and less in a second direction, the first and second cross sections being perpendicular to each other.

9. The apparatus of claim 1, wherein an F-number of the apparatus objective is in a range 1 to 0.5.

10. The apparatus of claim 1, wherein the spherical aberration of the apparatus objective is configured to separate focuses of axial rays and peripheral rays of the illumination and imaging in a range from one millimeter to 10 millimeters in a direction of the optical axis.

11. The apparatus of claim 8, wherein a diameter of the entrance pupil of the apparatus objective in the first direction is larger than a diameter of the entrance pupil of the apparatus objective in the second direction which is perpendicular to the first direction.

12. The apparatus of claim 1, wherein the apparatus objective comprises a first spherical lens and a second spherical lens; the first spherical lens having a shape factor from −3 to −0.5 and being located in front of the second spherical lens in the direction of imaging; and
    the second spherical lens having a shape factor from −2 to 0.5, the focal length of the second spherical lens being larger than that of the first spherical lens.

13. The apparatus of claim 1, wherein the apparatus objective comprises at least one non-spherical lens.

14. A method of non-contact examination of an eye, the method comprising
    illuminating and imaging an eye through a common apparatus objective which has a positive optical power and a positive spherical aberration for covering an angle wider than a cross section of the zone I of the retinal vasculature, the imaging and the illumination having optical paths deviated from each other in the examination apparatus;
    distorting an image of an exit pupil of imaging and an image of an entrance pupil of illumination on their image planes within the eye by the positive spherical aberration of the apparatus objective;
    separating the optical paths of the imaging and illumination at least on frontal and rear surfaces of the crystalline lens by the deviation of the optical paths from each other in the examination apparatus, cross sections of the optical paths on the frontal and rear surfaces of the crystalline lens being fully illuminated areas side by side; and
    modifying, by a secondary lens unit located behind the apparatus objective in the optical path in a direction of the imaging at least one of the following optical features: lateral color aberration, astigmatism, field curvature and coma caused by the apparatus objective; and
focusing the imaging radiation modified by the secondary lens unit on an image sensor for forming an image of a retina of the eye.

15. The apparatus of claim 1, wherein the optical path of the imaging is separate from the optical path of illumination.

* * * * *